United States Patent [19]
Walters et al.

[11] Patent Number: 5,545,760
[45] Date of Patent: Aug. 13, 1996

[54] PROCESS FOR MAKING FLUORENONES

[75] Inventors: Marlin E. Walters, West Columbia; Richard P. Kolonko; Richard M. Wehmeyer, both of Lake Jackson, all of Tex.

[73] Assignee: The Dow Chemical Company, Midland, Mich.

[21] Appl. No.: 384,908

[22] Filed: Feb. 7, 1995

[51] Int. Cl.$^6$ .................................................. C07C 45/36
[52] U.S. Cl. .................................................. 568/321
[58] Field of Search .................................................. 568/321

[56] References Cited

U.S. PATENT DOCUMENTS

| | | | |
|---|---|---|---|
| 3,875,237 | 4/1975 | Niznik | 568/321 |
| 4,009,151 | 2/1977 | Pearson et al. | 568/321 |
| 4,218,400 | 8/1980 | Finger | 568/321 |
| 4,297,514 | 10/1981 | Ma | 568/321 |

FOREIGN PATENT DOCUMENTS

| | | | |
|---|---|---|---|
| 2142217 | 1/1971 | France | 568/321 |
| 198668B | 12/1983 | Hungary | 568/321 |
| 79/144348 | 11/1979 | Japan | 568/321 |

OTHER PUBLICATIONS

Kinoshita et al., "Liquid Phase Air Oxidation of Fluorene, Part 1. Effects of Alkali and Pyridine," *Nippon Kagaku Zasshi*, vol. 80 (1959), pp. 206–208 (translation attached).

Sprinzak, "Reactions of Active Methylene Compounds in Pyridine Solution. I. The Ionic Autoxidation of Fluorene and its Derivatives," *J. Am. Chem. Soc.*, vol. 80 (1958), pp. 5449–5455.

*Primary Examiner*—James H. Reamer

[57] ABSTRACT

A process for the oxidation of a fluorene compound to a corresponding fluorenone compound comprises treating the fluorene compound with an oxidizing gas in the presence of a solid alkali metal or alkaline earth metal oxide or hydroxide or a concentrated aqueous solution thereof in a reaction mixture in a non-aqueous heterocylic nitrogenous solvent, wherein the reaction mixture is free of a phase transfer agent, for a time sufficient and at a temperature sufficient to convert the fluorene compound to the fluorenone compound.

31 Claims, No Drawings

PROCESS FOR MAKING FLUORENONES

TECHNICAL FIELD

This invention relates to a simple, highly selective process for the oxidation of fluorenes to corresponding fluorenones. Fluorenones, particularly 9-fluorenone, are valuable intermediates for the preparation of intermediates for making condensation polymers, such as 9,9-bis-(4-hydroxyphenyl)fluorene, which is used in making polycarbonate and epoxy resins.

BACKGROUND ART

Finger (U.S. Pat. No. 4,218,400), herein incorporated by reference, has recited oxidizing fluorene to fluorenone by air or oxygen, in the presence of a quaternary salt in a two-phase system, containing a water-immiscible solvent and aqueous alkali metal hydroxide solution.

Kinoshita et al., "Liquid Phase Air Oxidation of Fluorene. Part 1. Effects of Alkali and Pyridine," *Nippon Kagaku Zasshi*, vol. 80 (1959), pages 206–208, have proposed oxidation of fluorene to fluorenone in a mixed solution of pyridine and aqueous sodium hydroxide solution (about 1N) at about 95° C. The conversion to fluorenone is of the order of 50 percent.

Pearson et al. (U.S. Pat. No. 4,009,151), herein incorporated by reference, have proposed the oxidation of 2-vinylfluorene to 2-vinylfluorenone in a dilute solution in pyridine, containing a small amount of benzyltrimethyl ammonium chloride.

Niznik (U.S. Pat. No. 3,875,237) has proposed preparing fluorenone from fluorene by oxidation with molecular oxygen in dimethylsulfoxide, using a small amount of an alkali metal hydroxide, at temperatures from ambient to about 100° C.

Hiiro et al. (JP Kokai 79/144,348, *Chem. Abs.* 92:215069q) have proposed oxidizing aromatic or heterocyclic methylene compounds, including diphenylmethane, anthracene and fluorene, in the presence of alkali in 1,3-dimethylimidazolidinone.

Sprinzak, "Reactions of Active Methylene Compounds in Pyridine Solution. I. The Ionic Autoxidation of Fluorene and its Derivative, *J. Am. Chem. Soc.*, vol. 80 (1958), pages 5449–5455, have disclosed oxidation of fluorenes to fluorenones in pyridine solution in the presence of benzyltrimethyl ammonium hydroxide.

Szeverenyi et al. (HU 198,668B) have proposed preparing 9-fluorenone from fluorene by oxidation with air or oxygen in a solvent in the presence of a quaternary ammonium salt and potassium hydroxide at low temperatures.

Knoche (FR 2,142,217, *Chem. Abs.* 79:50398a) recites the oxidation of fluorene to fluorenone in the presence of a saturated solution of KOH or NaOH in polyether solvents.

Ma (U.S. Pat. No. 4,297,514), herein incorporated by reference, recites the oxidation of compounds, having activated methylene radicals in a multiphase system containing a synergistic combination of elemental carbon and a phase-transfer catalyst.

Although the processes disclosed heretofore give oxidation products, there is a continuing need for processes for oxidizing fluorenes to fluorenones, characterized by high reaction rates, high yields and ease of separating the thus-produced fluorenones. In particular known methods of oxidizing fluorene to fluorenone are not selective for fluorene when the fluorene starting material is impure, containing other oxidizable hydrocarbons, e.g. diphenylmethane. When compounds other than fluorenone are produced in such oxidations, separation from fluorenone is difficult. It would, therefore, desirable to have an oxidation process selective for formation of fluorenone.

It an object of this invention to provide a fast, selective process for making fluorenones from fluorene, wherein the thus-produced fluorenones are readily isolated from the reaction mixtures.

DISCLOSURE OF INVENTION

This invention relates to process for the oxidation of a fluorene compound to a corresponding fluorenone by treating the fluorene compound with an oxidizing gas in the presence of a solid alkali metal or alkaline earth metal oxide or hydroxide or a concentrated aqueous solution thereof in a reaction mixture in a heterocyclic nitrogenous solvent, wherein the reaction mixture is free of a phase transfer agent, for a time sufficient and at a temperature sufficient to convert the fluorene compound to the fluorenone compound.

DETAILED DESCRIPTION

The conversion of fluorene compounds to corresponding fluorenone compounds can be represented by the general equation:

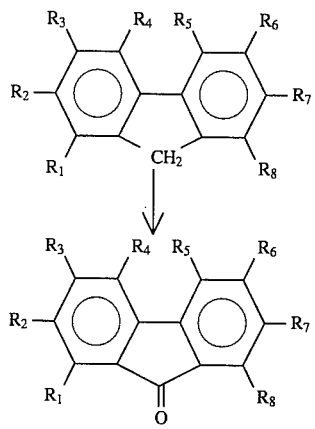

wherein each of $R_1$–$R_8$ is independently selected from hydrogen or substituents which are inert under the reaction conditions employed. The substituents can advantageously include hydrocarbyl, hydrocarbyloxy, nitro, amino, substituted amino, cyano, formyl, keto, hydroxy, carboxy, carboxyalkyl, alkyloxycarbonyl, halogen, etc.

Hydrocarbyl includes alkyl, cycloalkyl, aryl, arylalkylene (aralk), alkylcyloaliphatic and alkylenecycloalkyl, that is, functions containing carbon and hydrogen atoms. Hydrocarbyl functions include both saturated and unsaturated substituents. Aryl includes mono- and polycyclic aromatic substituents, e.g. phenyl, biphenyl, biaryl, naphthyl, phenanthrenyl, anthracenyl or other aryl groups, including those connected to a fluorene ring structure by an alkylene group. Alkylaryl residues include alkyl, alkenyl and alkynyl-substituted aryl substituents. Aralkyl includes alkyl, alkenyl or alkynyl groups, substituted by one or more aryl groups.

Alkyl groups include both straight- and branched-chain isomers of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, nonadecyl and eicosyl groups, as well as the corresponding unsaturated (alkenyl or alkynyl) groups and higher homologues. Preferably, the alkyl groups are of 1–20 carbon atoms, more preferably of 1–5 carbon atoms, most preferably those of 1–3 carbon atoms. Alkyl of 1–5 carbon atoms includes the various methyl, ethyl, propyl, butyl and pentyl isomers.

Alkyl, aryl, alkaryl and aralkyl substituents are suitable hydrocarbyl substituents on the fluorene reactant.

Other inert substituents include, but are not limited to alkoxy, aryloxy or alkaryloxy, wherein alkoxy includes methoxy, ethoxy, propyloxy, butoxy, pentoxy, hexoxy, heptoxy, octyloxy, nonyloxy, decyloxy and polyoxyethylene, as well as higher homologues; aryloxy, phenoxy, biphenoxy, naphthyloxy, etc. and alkaryloxy includes alkyl, alkenyl and alkynyl-substituted aryl.

Additional inert substituents include halo, such as bromo, chloro or iodo.

In addition, substituents at adjacent positions on the aromatic rings of fluorene can together form additional carbocyclic or heterocyclic rings, e.g., benzofluorenes, dibenzofluorenes, pyridofluorenes, etc. More specifically, if any combination of $R_1$–$R_2$, $R_2$–$R_3$ or $R_3$–$R_4$ is —CH=CH—CH=CH—, the starting fluorene is a benzofluorene.

Most preferably, the fluorene starting material is fluorene itself, that is, a compound of the general formula in which each of $R_1$–$R_8$ is H.

The process of this invention has been found to be particularly advantageous for the selective oxidation of fluorene in a material, identified as "crude fluorene concentrate," which contains about 45–65 percent of fluorene, along with dimethylbiphenyl, trimethylbiphenyl, acenaphthene, methylacenaphthene, trimethylnaphthalenes, and the like. A representative fluorene concentrate contains 57–60 percent of fluorene and is a clear solid, melting about 60° C. This material is advantageously stored in a tank, heated to about 80° C., and pumped to a mixer or reactor.

It has been found that application of the process of this invention to a crude fluorene concentrate produces an oxidate, in which fluorenone and substituted fluorenones are the sole oxygenated products. It is therefore believed that the process of this invention is useful for the oxidation of "acidic" hydrocarbons, that is, those having a pKa of about 21, particularly fluorenes, dihydroanthracene, xanthene or indene. Although the invention is explained in terms of fluorene, it applies to such acidic hydrocarbons as well. Less acidic hydrocarbons, e.g. diphenylmethane (pKa≈32), are not oxidized. The process of this invention therefore provides a highly selective process for making valuable intermediates without requiring extensive purification of crude concentrates, particularly fluorene concentrate, used as the starting material. Thus, the process of the invention includes a process of (a) using as a starting material a crude fluorene (having less than about 80 weight percent fluorene with a measurable amount, preferably at least about 0.1 weight percent diphenylmethane, other oxidizable hydrocarbon, preferably having a pKa of greater than about 32 or mixtures thereof) (b) treating the starting material with an oxidizing gas in the presence of a solid alkali metal or alkaline earth metal oxide or hydroxide or a concentrated aqueous solution thereof in a reaction mixture containing a heterocylic nitrogenous solvent, wherein the reaction mixture is free of a phase transfer agent, for a time sufficient and at a temperature sufficient to convert the fluorene compound to the fluorenone compound, to produce a crude fluorenone and (c) recovering an oxidized product which is preferably at least about 98 weight percent pure oxidized acidic hydrocarbon (preferably fluorenone) alternatively (d) using the crude fluorenone as a starting material for a subsequent reaction. Subsequent reactions of fluorenone and other oxidized acidic hydrocarbons such as indenone, xanthenone, and anthraquinone are known to those skilled in the art. For instance fluorenones are reacted with phenols under the influence of an acidic catalyst to form bis(hydroxyphenyl) fluorenes. Since the desired ketone, fluorenone, is formed selectively, there are fewer by-products to separate from the reaction product of the subsequent reaction than would be present if a less selective process were used and more oxidation by-product (e.g. diphenylketone for diphenylmethane) were formed in the oxidation step (b).

The oxidations are carried out in a reaction mixture containing a heterocyclic nitrogenous solvent, e.g., pyridine, the lutidines, the picolines and diazines, e.g., pyrazine or pyridazine. Many of the foregoing compounds, for example, pyridine, 2,3-lutidine, 3-picoline, 4-picoline, pyrazine and pyridazine, are miscible with water in all proportions. Less soluble members of the group of useful heterocyclic nitrogenous solvents, e.g. 2,4-lutidine or 2,5-lutidine, are soluble in water to the extent of 20 g or more/100 mL. Advantageously, the solvents are free of functionality such as carbonyl or hydroxy. It is preferred to carry out the process of this invention in heterocyclic nitrogenous solvents, which have a water solubility above about 20 g/100 mL at 25° C.

Preferred solvents for the practice of this invention will conveniently be selected from pyridine, the picolines and the lutidines, including alkylamino derivatives thereof. Most preferably, the process is done using pyridine.

Advantageously, and preferably, the process of this invention is carried out in the substantial absence of organic solvents, other than the above-disclosed heterocyclic nitrogenous solvent or solvents. Substantial absence refers to absence except for inadvertent impurities which may be solvents, particularly impurities such as hydrocarbons in crude fluorene starting materials.

The process is carried out using weight ratios of fluorene compound to heterocyclic nitrogenous solvent from about 3:1 to about 1:100. The minimum amount of heterocyclic solvent, useable in the process of this invention, is determined by the solubility of the fluorene compound in the solvent. If a solution of fluorene is to be used, the minimum amount of solvent is that in which the fluorene compound forms a saturated solution. In some cases, it may be advantageous to use a suspension/slurry of fluorene in the heterogeneous nitrogenous solvent. The solubility of fluorene in pyridine is about 25 percent by weight at about 25° C. Preferably, weight ratios from about 3:1 to about 1:25 are employed, most preferably from about 1:3 to about 1:15.

It will also be understood the reaction mixtures can contain inert materials, which are normally hydrocarbonaceous. For example, crude fluorene concentrate contains aromatic hydrocarbons, which are not oxidized under the reaction conditions employed. It is also contemplated that small amounts of hydrocarbon diluents, e.g., toluene or diphenylmethane, could be added to the reaction mixtures.

Because small amounts of water are not detrimental to the process, the solvents used can be commercial grade materials. Neither extreme caution in handling the solvents nor extensive purification of the solvents is required.

"Alkali metal," as used in the specification and claims, includes lithium, sodium and potassium. "Alkaline earth metal," as used in the specification and claims, includes magnesium, calcium and barium. In addition to the oxides and hydroxides of the foregoing metals, it is contemplated that the carbonates can also be used in the practice of this invention, alone or admixed with the oxide or hydroxides.

The alkali metal or alkaline earth metal oxide or hydroxide, or mixture thereof, can advantageously be used in solid form, e.g. powders or pellets. Highly soluble compounds are preferably used in concentrated aqueous solutions, containing a maximum of about 50 percent to about 75 percent by weight of water. When an aqueous solution is used, it is preferred to use a highly concentrated (above about 40 percent by weight of solute) or saturated solution. Saturated solutions of sodium hydroxide or potassium hydroxide contain about 50 percent of water, depending upon the temperature. Such solutions are conveniently used in the process of the invention. It is particularly advantageous, in using concentrated aqueous solutions, particularly of sodium or potassium hydroxide, to use ratios of sodium or potassium hydroxide solution to heterocyclic nitrogenous solvent such that two liquid phases are present in the reaction. Such ratios are readily determined by routine experimentation.

Solid forms of the alkali metal or alkaline earth metal oxides or hydroxides generally contain some water. Potassium hydroxide pellets normally contain about 15 percent by weight of water. Sodium hydroxide pellets commonly contain about 2 percent by weight of water. Sodalime commonly contains 6–18 percent by weight of water. Although it is desirable to control the amount of water in the reaction mixtures and it is well known that alkali metal and alkaline earth metals oxides and hydroxides are hygroscopic, it is not necessary to use stringent precautions to handle even the hygroscopic alkali metal or alkaline earth metals oxides or hydroxides, used in the reaction mixtures.

It will be understood that the alkali metal or alkaline earth metal oxide or hydroxide is not consumed during the process. Therefore, it is feasible in some instances to recycle the oxide or hydroxide in successive runs, whether batch or continuous. Recycling the oxide or hydroxide is particularly advantageous when the reaction mixture separates into two phases and the aqueous layer, containing hydroxide solution can be removed and recycled, at least until the solution becomes diluted with excessive amounts of by-product water. When dilute, the concentration of hydroxide is optionally adjusted by addition of solid or more concentrated hydroxide solution, and the solution is suitable for use yet again.

To attain high conversions and fast reactions, it has been found that the use of large amounts of alkali metal or alkaline earth metals oxides or hydroxides, with respect to fluorene compound, is advantageous. Although the use of small amounts of alkali metal or alkaline earth metal oxide or hydroxides is operable, the use of small amounts of these materials may result in an unacceptably slow reaction rate. Molar ratios of oxide/hydroxide to fluorene compound from about 0.01:1 to about 20:1 are operable. Preferably, molar ratios of oxide/hydroxide to fluorene compound are from about 1:1 to about 15:1. Most preferably, the ratios are from about 5:1 to about 15:1.

The process of the invention is operable over a wide range of water concentrations. Whereas it is preferred that the pyridine phase be stirred with an aqueous solution of base, the oxidations have also been carried out successfully at water concentrations of about 300 ppm and are feasible at even lower water levels.

It will be understood that the water can be introduced into the reaction mixture by the alkali metal or alkaline earth metal oxide or hydroxide, by the heterocyclic nitrogenous solvent and/or by the fluorene compound being oxidized. In addition, water is a byproduct of the reaction.

The oxidizing gas is selected from oxygen or air or mixtures thereof. It is preferred to use oxygen or air/oxygen mixtures in the practice of this invention. Oxygen or air is optionally admixed with inert (non-oxidizing) gases such as nitrogen.

The process of this invention can be carried out under ambient pressure (about 1 bar (100 kPa)) or under elevated pressures. Preferably, the process is carried out using oxygen as the oxidizing gas, under pressures from about 1 bar (100 kPa) to about 10 bars (1000 kPa). To conveniently avoid explosive mixtures air is alternativley preferably used at these pressures.

The process of this invention is carried out at moderate temperatures, advantageously from about 0° C. to about 75° C. Preferably, the process is carried out from about 10° C. to about 65° C.

Depending upon the conditions selected, quantitative conversion of fluorene compounds to corresponding fluorenones is accomplished rapidly, within reaction times of 1–6 hours in batch mode processes.

Oxygen consumption during the process depends upon the conditions selected. In some cases, most of the oxygen is consumed. In others, significant excesses of oxygen are required for complete conversion of fluorenes to fluorenones. The exact conditions are readily determined by routine experimentation.

The process of this invention can be carried out in any type of reactor, which is not attacked under the reaction conditions and which does not interact deleteriously with the reactants, solvent or products. Accordingly, the process can be carried out in glass reactors, stainless steel reactors, fluorocarbon lined reactors, and tubes or pipes lined with glass, plastic or rubber.

The reactors are advantageously provided with stirring means, or the reactors are advantageously rocked or shaken to provide contact between the materials in the reaction mixture. Alternativley or simultaneously, it is advantageous to provide agitation by use of a circulating pump. Preferably there is a stirring means, e.g. impeller, in the organic phase.

The process of this invention can be done in batch or continuous mode. Continuous reactions can be done in cocurrent flow mode, countercurrent flow mode or crosscurrent flow mode, of which cocurrent flow mode, corresponding to plug flow conditions, is preferred when appropriate equipment is more readily available. Continuous reactions can also be done in stirred tank reactors or packed or agitated column reactors, of which the latter are preferred.

Another preferred embodiment is to carry out the process of this invention in continuous mode, using a column packed with sodium hydroxide or potassium hydroxide solids, preferably pellets. The continuous process is preferably done using oxygen as the oxidizing gas, preferably under pressure from ambient to about 10 bars.

In another preferred continuous mode of operation, the oxidations are carried out in countercurrent flow mode, using a stream of fluorene compound in heterogeneous nitrogenous solvent flowing in a direction opposite to streams of air/oxygen and a concentrated aqueous solution of alkali metal hydroxide.

Another preferred embodiment is a batch process of the invention wherein the oxidizing gas is introduced under pressure into a stirred reactor containing a continuous organic phase containing droplets of aqueous sodium or potassium hydroxide.

Unlike many of the processes reported for the oxidation of fluorenes to fluorenones, the process of this invention does not require the inclusion of a phase transfer agent or phase transfer catalyst in the reaction mixtures. Materials falling within this definition are generally quaternary salts, e.g.

quaternary ammonium or phosphonium salts. The use of phase transfer agents/catalysts has been set forth by Ma, Szeverenyi et al., Finger and Pearson, supra.

An advantageous feature of the process of this invention is the ease with which the fluorenone product can be isolated. If after removal of solids the reaction mixture appears as one phase, solvent is removed from the mixture, for example, using a rotary evaporator. The residue from which solvent has been removed is cooled to induce crystallization of fluorenone compound and crystalline fluorenone product is removed by filtration. Extremely high purity fluorenone can be isolated by washing the crude crystalline fluorenone with solvents such as hydrocarbon solvents, preferrably aliphatic more preferably having from about 5 to about 7 carbon atoms or alcohol solvents, preferably having from 1 to 6 carbon atoms, most preferably hexane, cyclohexane, isopropanol, methanol, or ethanol.

If the reaction mixture, at the end of the reaction, has split into two phases, the water layer is preferably separated and discarded or recycled. The organic layer, containing the fluorenone product, is processed as explained for the one phase reaction mixture.

The facile separation of fluorenone products from the oxidation mixtures is particularly advantageous, because crude fluorene-containing concentrates need not be purified before the oxidation to fluorenone by the practice of the invention.

In a particularly preferred aspect, the process of this invention is one wherein the process is carried out in continuous mode in a column packed with potassium hydroxide solids, preferably pellets, the oxidizing gas is oxygen under a pressure from ambient to about 10 bars (1000 kPa), the heterocyclic nitrogenous solvent is pyridine, the fluorene compound is fluorene or a crude fluorene concentrate and the temperature is from about 20° C. to about 45° C.

Another highly preferred embodiment is a batch process of the invention wherein the oxidizing gas is introduced under pressure into a stirred reactor containing a continuous organic phase containing droplets of aqueous sodium or potassium hydroxide wherein the aqueous solution is at least about 40 percent by weight potassium hydroxide; the oxidizing gas is air, and the temperature is from about 40° C. to about 65° C.

In another highly preferred aspect, the process of this invention is that carried out in continuous mode in a stirred reactor, wherein a solution of fluorene or crude fluorene concentrate in pyridine is contacted in countercurrent flow mode with an aqueous solution of at least about 40 percent by weight of sodium or potassium hydroxide, the oxidizing gas is a mixture of air and oxygen, and the temperature is from about 40° C. to about 65° C.

Without further elaboration it is believed that one skilled in the art can, using the preceding description, utilize the present invention to the fullest extent. The following preferred specific embodiments are, therefore, to be construed as merely illustrative and not limitative of the remainder of the disclosure in any way whatsoever.

In the following examples, the temperatures are set forth in degrees Celsius. Unless otherwise indicated, all parts and percentages are by weight. Unless otherwise noted, the results of gas chromatography (GC) analyses are in percent by weight.

EXAMPLE 1

OXIDATION OF FLUORENE

The reaction is done in a 1000-mL cylinder (100 mm in diameter, 140 mm in height), equipped with a 50 mm diameter turbine impeller driven by a vertical shaft. The stirring rate is measured by a tachometer. The temperature is controlled by a 3.04 meter by 0.635 cm external diameter coil, immersed in the reaction medium, through which coolant, maintained at a constant temperature by a circulating refrigerated/heated bath, is pumped. The temperature is measured by a thermocouple inside a thermowell which runs the entire depth of the reactor. The reactor is also equipped with a nitrogen inlet which is used to maintain a nitrogen atmosphere above the reaction mixture. The entire apparatus is constructed of fluorocarbon resin commercially available from E. I. du Pont de Nemours & Co. under the trade designation Teflon PFA.

The reactor is flushed with nitrogen and KOH (85 percent, contains 15 percent water, A.C.S reagent grade, 39.0 g, 0.59 mole, crushed in a mortar with pestle), followed by a solution consisting of fluorene (34.00 g, 0.205 mole) and pyridine (291.6 g, 3.686 mole, 304.0 mL) is charged to the reactor. The stirrer is started and the speed adjusted to 700 rpm. The coolant is admitted to the coils and the temperature of the reaction solution is adjusted to 15° C. The air flow is started and adjusted to 2831.60 mL/min as measured by a rotometer. The start of the air flow is considered to be time 0 for the reaction. The reaction mixture is sampled after 10 min and analyzed by gas chromatography (GC) on a Varian 3400 GC equipped with a 30 meter by 0.53 mm Megabore (Trademark of J & W Scientific Inc.) capillary column coated with a 3 micron film of DB-624 as the stationary phase and a flame ionization detector (FID, Varian 3400). At this point, the reaction mixture contains 79.47 percent by weight of fluorene and 20.53 percent of 9-fluorenone. The reaction mixture, sampled again after four hours and analyzed as before, contains 10.75 percent by weight of fluorene and 89.25 percent by weight of 9-fluorenone.

EXAMPLE 2

OXIDATION USING 85 percent POTASSIUM HYDROXIDE; EFFECT OF IMPROVED AIR DISPERSION WITH A FASTER STIRRING RATE The reactor, described in Example 1, is flushed with nitrogen. Potassium hydroxide (85 percent, contains 15 percent water, A.C.S reagent grade, 39.0 g, 0.59 mole, crushed in a mortar with pestle) is charged to the reactor, followed by a solution of fluorene (54.08 g, 0.325 mole) and pyridine (216.3 g, 2.73 mole, 221 mL). The stirrer is started and the speed adjusted to 1500 rpm. The coolant is admitted to the coils and the temperature of the reaction mixture is adjusted to 30.4° C. The air flow is started and adjusted to 943.87 mL/min (0.008826 mole/minute of contained oxygen) as measured by a rotometer. The start of the air flow is considered to be time 0 for the reaction. The reaction mixture is sampled after 60 minutes and analyzed by gas chromatography (GC) on a Varian 3400 GC equipped with a 30 meter by 0.53 mm Megabore (Trademark of J & W Scientific Inc.) capillary column coated with a 3 micron film of DB-624 as the stationary phase and a flame ionization detector (FID, Varian 3400). This analysis shows that the reaction mixture contains 35.33 percent by weight of fluorene, and 64.67 percent by weight of 9-fluorenone. The reaction mixture, sampled after three hours' reaction time, contains no detectable fluorene, and 100 percent of 9-fluorenone.

The stirring is stopped and the phases allowed to separate. The organic phase is decanted and placed on the rotary evaporator to remove pyridine to less than 0.5 percent of the mass (by GC). The resulting oil is allowed to cool to 25° C. and the resulting crystals of fluorenone are collected on a fritted filter. The dried crystals weigh 57.85 g (98.67 percent of theory). The oxygen content of the gas stream is 1.58 mole of oxygen (in 226,528 mL of air passing through the reactor during the three hour reaction time).

This example shows that increased stirring rate results in increased utilization of the oxygen.

EXAMPLE 3

OXIDATION USING 85 percent POTASSIUM HYDROXIDE AS THE BASE; EFFECT OF IMPROVED AIR DISPERSION WITH A FASTER STIRRING RATE The reactor of Example 1 is flushed with nitrogen. Potassium hydroxide (85 percent, contains 15 percent water, A.C.S reagent grade, 39.0 g, 0.59 mole, crushed in a mortar with pestle) is charged to the reactor, followed by a solution consisting of fluorene (54.08 g, 0.325 mole) and pyridine (216.3 g, 2.73 mole, 221 mL). The stirrer is started and the speed adjusted to 2000 rpm. The coolant is admitted to the coils and the temperature of the reaction mixture is adjusted to 30.4° C. The air flow is started and adjusted to 943.87 mL/min (0.008826 mole/minute of contained oxygen) as measured by a rotameter. The start of the air flow is considered to be time 0 for the reaction.

The reaction mixture, sampled after 60 minutes and analyzed by gas chromatography (GC, Varian 3400 GC equipped with a 30 meter by 0.53 mm Megabore [Trademark of J & W Scientific Inc.] capillary column coated with a 3 micron film of DB-624 as the stationary phase and a flame ionization detector (FID, Varian 3400). The reaction mixture contains 14.13 percent by weight of fluorene and 5.87 percent by weight of 9-fluorenone. After two hours' reaction, the reaction mixture contains no detectable fluorene and 100 percent of 9-fluorenone.

The stirring is stopped and the phases are allowed to separate. The organic phase is removed by decantation and placed on a rotary evaporator to remove pyridine to less than 0.5 percent of the mass by GC. The resulting oil is allowed to cool to 25° C. and the crystals of fluorenone are collected on a fritted filter. The dried crystals weigh 65.31 g (100.4 percent of theory). The amount of oxygen in air passed through the reactor during the reaction is 1.05 mole of oxygen.

This example shows that increasing the stirring rate results in increased utilization of the oxygen feed.

EXAMPLE 4

OXIDATION METHOD USING 85 percent POTASSIUM HYDROXIDE PELLETS AS THE BASE; THE EFFECT OF USING OXYGEN IN PLACE OF AIR The reactor of Example 1 is flushed with nitrogen. Potassium hydroxide pellets (85 percent, contains 15 percent water, A.C.S reagent grade, 29.4 g, 0.45 mole) are charged to the reactor, followed by a solution consisting of fluorene (29.4 g, 0.177 mole) and pyridine (294.0 g, 3.717 mole, 300 mL). The stirrer is started and the speed adjusted to 800 rpm. The coolant is admitted to the coils and the temperature of the reaction solution is adjusted to 40.1° C. The oxygen flow is started and adjusted to 37.75 mL/min (0.1011 mole/hour of oxygen) as measured by a rotameter. The start of the oxygen flow is considered to be time 0 for the reaction.

The reaction mixture, sampled and analyzed after 60 min, as described in Example 3, contains 14.78 percent by weight of fluorene and 85.22 percent by weight of 9-fluorenone. The reaction mixture, sampled again after two hours and analyzed as before, contains no detectable fluorene and 100 percent by weight of 9-fluorenone. The amount of oxygen passed through the reactor is 0.202 mole of oxygen. The fluorenone product is isolated as in Example 3.

EXAMPLE 5

OXIDATION USING 98 percent SODIUM HYDROXIDE PELLETS AS THE BASE

The reactor, described in Example 1, is flushed with nitrogen. To the reactor is charged NaOH pellets (98.4 percent, A.C.S reagent grade, 29.4 g, 0.736 mole) followed by a solution consisting of fluorene (29.4 g, 0.177 mole) and pyridine (294.0 g, 3.717 mole, 300 mL). The stirrer is started and the speed adjusted to 800 rpm. The coolant is admitted to the coils and the temperature of the reaction solution is adjusted to 40.1° C. The oxygen flow is started and adjusted to 37.75 mL/min (0.1011 mole/hour of oxygen), as measured by a rotameter. The start of the oxygen flow is considered to be time 0 for the reaction. The reaction mixture, sampled after 60 minutes and analyzed by gas chromatography as in Example 3, contains 24.09 percent fluorene, and 75.91 percent of 9-fluorenone. The reaction mixture, after 2 h, 20 minutes, contains no detectable fluorene and 100 percent of 9-fluorenone. The amount of oxygen, passed through the reaction mixture is 0.232 mole of oxygen. The fluorenone product is isolated as in Example 3.

EXAMPLE 6

OXIDATION USING 50 percent SODIUM HYDROXIDE SOLUTION AS THE BASE

The reactor of Example 1 is flushed with nitrogen, as above. To the reactor is charged NaOH (sodium hydroxide) solution (50 percent aqueous, A.C.S reagent grade, 29.4 g dry weight 58.8 g solution weight, 0.736 mole), followed by a solution consisting of fluorene (29.4 g, 0.177 mole) and pyridine (294.0 g, 3.717 mole, 300 mL). The stirrer is started and the speed adjusted to 800 rpm. The coolant is admitted to the coils and the temperature of the reaction mixture is adjusted to 40.1° C. The oxygen flow is started and adjusted to 37.75 mL/min (0.1011 mole/hour of oxygen) as measured by a rotameter. The start of the oxygen flow is considered to be time 0 for the reaction.

The reaction mixture is sampled and analyzed as in Example 3. After 60 min, the mixture contains 31.10 percent of fluorene, and 68.90 percent of 9-fluorenone. The reaction mixture, sampled again after 2 h, 30 min, contains 1.84 percent of fluorene and 98.16 percent of 9-fluorenone. After 4 h, 30 min, the mixture contains no detectable fluorene and 100 percent of 9-fluorenone. The amount of oxygen, passed through the reaction mixture is 0.455 mole of oxygen. The product is isolated as in Example 3.

EXAMPLE 7

OXIDATION USING SODA LIME AS THE BASE

The reactor of Example 1 is flushed with nitrogen. To the reactor is charged soda lime (4 to 8 mesh, Certified A.C.S., 29.4 g, entry no. 8511, "The Merck Index," eleventh ed., 1989), followed by a solution consisting of fluorene (29.4 g, 0.177 mole) and pyridine (294.0 g, 3.717 mole, 300 mL). The stirrer is started and the speed adjusted to 800 rpm. The coolant is admitted to the coils and the temperature of the reaction solution is adjusted to 40.1° C. The oxygen flow is started and adjusted to 37.75 mL/min (0.1011 mole/hour of oxygen) as measured by a rotameter. The start of the oxygen flow is considered to be time 0 for the reaction.

The reaction mixture, sampled and analyzed as in Example 3, at 60 min contains 31.10 percent of fluorene and 67.28 percent of 9-fluorenone. At the end of 2 h, 30 min, the reaction mixture contains 4.21 percent of fluorene and 95.79 percent of 9-fluorenone. After 4 hr, 10 min, the reaction mixture contains no detectable fluorene and 100 percent of 9-fluorenone. The amount of oxygen, passed through the reaction mixture, is 0.420 mole of oxygen. The product is isolated as in Example 3.

EXAMPLE 8

OXIDATION USING CALCIUM HYDROXIDE AS THE BASE

The reactor of Example 1 is flushed with nitrogen. To the reactor is charged calcium hydroxide (powder, Certified USP, 29.4 g, 0.397 mole), followed by a solution consisting of fluorene (29.4 g, 0.177 mole) and pyridine (294.0 g, 3.717 mole, 300 mL). The stirrer is started and the speed adjusted to 800 rpm. The coolant is admitted to the coils and the temperature of the reaction solution is adjusted to 40.1° C. The oxygen flow is started and adjusted to 37.75 mL/min (0.1011 mole/hour of oxygen), as measured by a rotameter. The start of the oxygen flow is considered to be time 0 for the reaction.

A sample of the reaction mixture, after 60 min, analyzed as in Example 3, contains 98.41 percent of fluorene and 1.59 percent of 9-fluorenone. At the end of 90 min, the reaction mixture contains 97.02 percent of fluorene, and 2.98 percent of 9-fluorenone. The reaction is terminated at this point.

EXAMPLE 9

OXIDATION METHOD USING LITHIUM HYDROXIDE AS THE BASE

The reactor of Example 1 is flushed with nitrogen. To the reactor is charged lithium hydroxide (powder, 29.4 g, 1.228 mole), followed by a solution consisting of fluorene (29.4 g, 0.177 mole) and pyridine (294.0 g, 3.717 mole, 300 mL). The stirrer is started and the speed adjusted to 800 rpm. The coolant is admitted to the coils and the temperature of the reaction solution is adjusted to 40.1° C. The oxygen flow is started and adjusted to 37.75 mL/min (0.1011 mole/hour of oxygen), as measured by a rotameter. The start of the oxygen flow is considered to be time 0 for the reaction.

The reaction mixture is sampled and analyzed as in Example 3. After 60 min, the mixture contains 95.67 percent of fluorene and 4.33 percent of 9-fluorenone. At the end of 430 min, the reaction mixture contains 65.02 percent of fluorene and 34.98 percent of 9-fluorenone. The reaction is terminated at this point.

EXAMPLE 10

OXIDATION USING ALUMINA AS THE BASE

The reactor of Example 1 is flushed with nitrogen. To the reactor is charged alumina 4126 (0.1587 cm extrudate, 29.4 g), followed by a solution consisting of fluorene (29.4 g, 0.177 mole, 300 mL). The stirrer is started and the speed adjusted to 800 rpm. The coolant is admitted to the coils and the temperature of the reaction solution is adjusted to 40.1° C. The oxygen flow is started and adjusted to 37.75 mL/min (0.1011 mole/hour of oxygen), as measured by a rotameter. The start of the oxygen flow is considered to be time 0 for the reaction. The reaction mixture, sampled after 90 minutes and analyzed by gas chromatography as in Example 3, contains 97.40 percent of fluorene and 2.60 percent of 9-fluorenone. After 300 min, the reaction mixture contains 95.24 percent of fluorene, and 4.76 percent of 9-fluorenone. The reaction is terminated at this point.

EXAMPLE 11

OXIDATION USING TALC AS THE BASE

The reactor, described in Example 1, is flushed with nitrogen. To the reactor is charged talc (purified grade, powder, 29.4 g) followed by a solution consisting of fluorene (29.4 g, 0.177 mole) and pyridine (294.0 g, 3.717 mole, 300 mL). The stirrer is started and the speed adjusted to 800 rpm. The coolant is admitted to the coils and the temperature of the reaction solution is adjusted to 40.1° C. The oxygen flow is started and adjusted to 37.75 mL/min (0.1011 mole/hour of oxygen), as measured by a rotameter. The start of the oxygen flow is considered to be time 0 for the reaction.

The reaction mixture, sampled after 60 min. and analyzed by gas chromatography as in Example 3, contains 98.47 percent of fluorene and 1.53 percent of 9-fluorenone. After 204 min, reaction mixture contains 96.73 percent of fluorene and 3.27 percent of 9-fluorenone. The reaction is terminated at this point.

EXAMPLE 12

OXIDATION USING 50 percent SODIUM HYDROXIDE AS THE BASE WITH CRUDE FLUORENE CONCENTRATE (CONTAINS 55 percent OF FLUORENE)

The reactor of Example 1 is flushed with nitrogen. To the reactor is charged NaOH (50 percent, contains 50 percent water, A.C.S reagent grade, 60.1 g dry wt, 1.50 mole, 78.6 mL) followed by a solution consisting of fluorene concentrate (120.0 g of concentrate, 0.397 mole) and pyridine (483.8 g, 6.12 mole, 495 mL). The stirrer is started and the speed adjusted to 800 rpm. The coolant is admitted to the coils and the temperature of the reaction solution is adjusted to 38.4° C. The oxygen flow is started and adjusted to 37.75 mL/min (0.1011 mole/h), as measured by a rotameter. The start of the oxygen flow is considered to be time 0 for the reaction.

The reaction mixture, sampled after 60 minutes and analyzed by gas chromatography as in Example 3, contains 56.11 percent of the original fluorene; 43.89 percent of the original fluorene has been converted to 9-fluorenone. The reaction mixture, sampled again after four hours and analyzed as above, contains no detectable fluorene and 100 percent of the expected 9-fluorenone. No other oxidation products, derived from the other hydrocarbons present, are detected.

The stirring is stopped and the phases allowed to separate. The organic phase is decanted and placed in a rotary evaporator to remove pyridine (to less than 0.5 percent of the mass by GC). The resulting oil is allowed to cool to 25° C. and the crystals of fluorenone are collected on a fritted filter.

EXAMPLE 13

CONTINUOUS OXIDATION WITH AIR, USING POTASSIUM HYDROXIDE AS THE BASE

The reactor is a 2.54 cm diameter section of pipe, 60.9 cm in length, packed to a depth of a 55.8 cm with a bed of KOH pellets (85 percent, contains 15 percent water, A.C.S reagent grade, 337.3 g, 6.01 mole). The temperature is measured by a thermocouple inside a thermowell, running the entire length of the reactor. The reactor is also equipped with a gas inlet at the bottom, through which a nitrogen atmosphere is maintained, until the oxidation is begun. The gas is changed to air during the reaction period. A second inlet at the base of the reactor is used to introduce the reaction mixture at a constant rate by means of a metering pump. A feed reservoir 2 liters in volume is connected to the suction port of the metering pump. The entire apparatus is constructed of fluorocarbon resin commercially available from E. I. du Pont de Nemours & Co. under the trade designation Teflon PFA.

After the reactor is flushed with nitrogen, a solution containing 10.01 percent by weight of fluorene in pyridine (800.3 g) is charged to the feed reservoir. The metering pump is set to pump at 1.4 mL/min and energized to initiate flow of fluorene solution to the reactor. The air flow is started and adjusted to 707.90 mL/min (0.397 mole/h of contained oxygen), as measured by a rotameter. The start of the air flow is considered to be time 0 for the reaction.

The temperature, as measured by the thermocouple inside the thermowell, is 32.5° C. The reaction mixture is collected at the overflow of the reactor column and is sampled at intervals and analyzed as in Example 3 by GC.

After 160 min, the reaction mixture contains 90.64 percent of pyridine, 3.61 percent of fluorene, and 7.09 percent of 9-fluorenone (66.26 percent of the original fluorene converted to 9-fluorenone). After 330 minutes, the reaction mixture contains 90.49 percent of pyridine, 3.42 percent of fluorene, and 7.28 percent of 9-fluorenone (69.04 percent conversion of fluorene to 9-fluorenone).

The reaction is continued until all of the material in the feed reservoir has been consumed (1290 min). A sample of the reaction mixture, analyzed as in Example 3, contains 90.38 percent of pyridine, 3.15 percent of fluorene, and 7.55 percent of 9-fluorenone (70.56 percent conversion). No other oxidation products are detected. Results are given in Table I.

TABLE I

CONTINUOUS OXIDATION OF FLUORENE IN AIR

| Time min | Air mL/ min | Temp °C. | Feed g | Feed Rate g/min | Py* | Fl** | Fn*** | percent Conv. |
|---|---|---|---|---|---|---|---|---|
| 0 | 0 | 26.9 | 698.4 | 1.42 | 89.30 | 10.70 | 0.00 | 0.00 |
| 40 | 707.9 | 32.9 | 640.0 | 1.46 | 90.14 | 8.07 | 2.63 | 24.58 |
| 130 | 707.9 | 32.7 | 516.0 | 1.38 | 90.44 | 4.07 | 6.63 | 61.96 |
| 160 | 707.9 | 32.5 | 472.4 | 1.45 | 90.64 | 3.61 | 7.09 | 66.26 |
| 180 | 707.9 | 32.0 | 446.0 | 1.32 | 90.65 | 3.67 | 7.03 | 65.70 |
| 210 | 1415.8 | 33.1 | 404.2 | 1.39 | 90.69 | 3.83 | 6.87 | 64.21 |
| 230 | 1415.8 | 32.7 | 375.5 | 1.43 | 90.50 | 3.97 | 6.73 | 62.90 |
| 250 | 1415.8 | 32.3 | 348.1 | 1.37 | 90.62 | 4.00 | 6.70 | 62.62 |
| 270 | 1415.8 | 34.3 | 327.8 | 1.02 | 90.84 | 4.01 | 6.69 | 62.52 |
| 290 | 1415.8 | 35.3 | 308.4 | 0.97 | 90.53 | 3.99 | 6.71 | 62.71 |
| 310 | 1415.8 | 35.4 | 288.1 | 1.01 | 90.46 | 3.77 | 6.93 | 64.77 |
| 330 | 1415.8 | 35.2 | 269.2 | 0.95 | 90.49 | 3.42 | 7.28 | 68.04 |
| 1290 | OFF | | | | 90.38 | 3.15 | 7.55 | 70.56 |

*Py = pyridine
**Fl = fluorene
***Fn = fluorenone

EXAMPLE 14

CONTINUOUS OXIDATION USING OXYGEN AND POTASSIUM HYDROXIDE AS THE BASE

The reactor, described in Example 13, is used. The packed bed of catalyst contains KOH pellets (85 percent, contains 15 percent water, A.C.S reagent grade, 337.3 g, 6.01 mole)

The reactor is flushed with nitrogen, after which a solution containing 9.98 percent by weight fluorene in pyridine (401.0 g) is charged to the feed reservoir. The metering pump is set to pump at 1.0 mL/min and energized to pump solution to the reactor. The oxygen flow is started and adjusted to 377.54 mL/min (1.01 mole/h oxygen), as measured by a rotameter. The start of the oxygen flow is considered to be time 0 for the reaction. The temperature is 27.5° C.

The reaction mixture is collected at the overflow of the reactor column and analyzed as in Example 3. After 70 min, the reaction mixture contains 90.89 percent of pyridine, 0.79 percent of fluorene, and 10.06 percent of 9-fluorenone (92.72 percent of the original fluorene converted to 9-fluorenone). The reaction mixture is sampled again after 330 minutes and analyzed as above. The reaction mixture contains 90.89 percent of pyridine, 1.51 percent of fluorene, and 9.34 percent of 9-fluorenone (86.08 percent of the original fluorene converted to 9-fluorenone). The reaction is continued until all of the material in the feed reservoir has been consumed (400 min) and sampled again. The reaction mixture contains 90.73 percent of pyridine, 2.06 percent of fluorene, and 8.79 percent of 9-fluorenone (81.01 percent of the original fluorene converted to 9-fluorenone). No other oxidation products are detected. Results are given in Table II:

TABLE II

CONTINUOUS OXIDATION OF FLUORENE IN AIR

| Time min | Air mL/ min | Temp. °C. | Feed Wt. (g) | Rate[a] | GC Analysis Py[b] | Fl[c] | Fn[d] | percent Conv. |
|---|---|---|---|---|---|---|---|---|
| 0 | 377.5 | 25.3 | 814.2 | | 89.15 | 10.85 | 0.00 | 0.00 |
| 70 | 377.5 | 27.5 | 745.4 | 0.98 | 90.89 | 0.79 | 10.06 | 92.72 |
| 120 | 377.5 | 27.5 | 694.7 | 1.01 | 90.98 | 1.16 | 9.69 | 89.31 |
| 180 | 377.5 | 27.4 | 637.8 | 0.95 | 90.89 | 1.69 | 9.16 | 84.42 |
| 220 | 377.5 | 27.4 | 595.5 | 1.06 | 90.66 | 1.95 | 8.90 | 82.03 |
| 330 | 377.5 | 27.2 | 592.6 | 0.03 | 90.89 | 1.51 | 9.34 | 86.08 |
| 360 | 377.5 | 27.4 | 566.2 | 0.88 | 90.80 | 1.78 | 9.07 | 83.59 |
| 400 | 377.5 | 27.4 | 522.2 | 1.10 | 90.73 | 2.06 | 8.79 | 81.01 |

[a]Feed rate in g/min
[b]Py = pyridine
[c]Fl = fluorene
[d]Fn = fluorenone

EXAMPLE 15

CONTINUOUS OXIDATION USING POTASSIUM HYDROXIDE AS THE BASE WITH OXYGEN (AMBIENT PRESSURE)

The reactor is a 2.54 cm diameter, 182.8 cm in length equipped with a 60 inch (152.4 cm) packed bed containing KOH (85 percent, contains 15 percent water, A.C.S reagent grade, 758.9 g, 13.5 mole) The temperature is measured by a thermocouple inside a thermowell, running the entire length of the reactor. The reactor is also equipped with a gas inlet at the lower end, which is used to maintain a nitrogen atmosphere in the reaction solution until the reaction is begun. The gas inlet then delivers oxygen for the reaction. A second inlet at the base of the reactor is used to introduce the reaction mixture at a constant rate by means of a metering pump. There is a feed reservoir (10 L in volume), connected to the suction pore of the metering pump. The entire apparatus is constructed of type 316 stainless steel.

The reactor is flushed with nitrogen, whereupon a solution containing 11.28 percent by weight of fluorene in pyridine is charged to the feed reservoir. The metering pump is set to pump at 1.0 mL/min and energized to initiate flow of solution to the reactor. The oxygen flow is started and adjusted to 47.19 mL/min (1.01 mole/h oxygen), as measured by a rotameter. The start of the oxygen flow is considered to be time 0 for the reaction. The temperature, as measured by the thermocouple, is 23.6° C.

The reaction mixture is collected at the overflow of the reactor column and is sampled at intervals and analyzed as in Example 3 by GC. After 120 minutes, the reaction mixture contains 0.55 percent of fluorene, and 10.73 percent of 9-fluorenone (95.12 percent of the original fluorene converted to 9-fluorenone). The reaction mixture, after 260 min, contains 1.57 percent of fluorene and 9.71 percent of 9-fluorenone (86.08 percent of the original fluorene converted to 9-fluorenone). The reaction is continued until all of the material in the feed reservoir is consumed (380 min). At this point, the reaction mixture contains 3.00 percent of fluorene and 8.28 percent of 9-fluorenone (73.40 percent of the original fluorene converted to 9-fluorenone). No other oxidation products are detected. Results of the experiments are given in Table III.

TABLE III

CONTINUOUS OXIDATION USING OXYGEN GAS; AMBIENT PRESSURE

| Time | $O_2$ | Press*** | Temp | Feed | CG Analysis[a] | | | percent |
|---|---|---|---|---|---|---|---|---|
| min | mL/min | mm Hg | °C. | Wt. (g) | Rate[b] | Fl* | Fn** | Conversion |
| 0 | 0 | 760 | 21.1 | 586.2 |  | 11.28 | 0.00 | 0.00 |
| 120 | 47.19 | 760 | 23.6 | 483.6 | 0.86 | 0.55 | 10.73 | 95.12 |
| 200 | 47.19 | 760 | 22.7 | 440.2 | 0.54 | 0.27 | 11.01 | 97.61 |
| 260 | 47.19 | 760 | 23.7 | 353.5 | 1.45 | 1.57 | 9.71 | 86.08 |
| 320 | 47.19 | 760 | 24.1 | 259.4 | 1.57 | 2.45 | 8.83 | 78.28 |
| 380 | 47.19 | 760 | 24.6 | 162.6 | 1.61 | 3.00 | 8.28 | 73.40 |

[a]percent by weight
[b]g/min
*Fl = fluorene
**Fn = fluorenone
***760 mmHg = 101 kPa

EXAMPLE 16

CONTINUOUS OXIDATION USING POTASSIUM HYDROXIDE AS THE BASE; OXYGEN AT INCREASED PRESSURE

The reactor is a 2.54 cm diameter, section of stainless steel tube, 182.8 cm in length and packed to a depth of 152.4 cm with KOH pellets (85 percent, contains percent water, A.C.S reagent grade, 758.9 g, 13.5 mole). The temperature is measured by a thermocouple inside a thermowell, which runs the entire length of the reactor. The reactor is also equipped with a gas inlet at the base. A nitrogen atmosphere is maintained in the reaction solution until the reaction is begun, after which the gas inlet delivers oxygen for the reaction. A second inlet at the base of the reactor is used to introduce the reaction mixture at a constant rate by means of a metering pump. The feed reservoir (10 L in volume) is connected to the suction port of the metering pump. The entire apparatus is constructed of type 316 stainless steel.

The reactor is flushed with nitrogen before a solution containing 11.28 percent by weight of fluorene in pyridine is charged to the feed reservoir. The metering pump is set to pump at a rate of 1.0 mL/min and energized to begin flow of solution to the reactor. The oxygen flow is started and adjusted to 28.32 mL/min (0.076 mole/h oxygen), as measured by a rotameter. The start of the oxygen flow is considered to be time 0 for the reaction. The exit port of the reactor is restricted to maintain the pressure within the reactor at 2.75 bars (275 kPa). The temperature, as measured by the thermocouple, is 25.3° C.

The reaction mixture is collected at the overflow of the reactor column and is sampled at intervals and analyzed by GC, as in Example 3. After 154 min, the reaction mixture contains 2.30 percent of fluorene and 8.98 percent of 9-fluorenone (79.61 percent of the original fluorene converted to 9-fluorenone). The reaction is continued until all of the material in the feed reservoir is consumed (394 min). The reaction mixture contains 1.90 percent of fluorene and 9.38 percent of 9-fluorenone (83.16 percent of the original fluorene converted to 9-fluorenone). No other oxidation products are detected. Results for the run are given in Table IV.

TABLE IV

OXIDATION OF FLUORENE WITH OXYGEN AT ELEVATED PRESSURE

| Time | $O_2$ | Press.*** | Temp. | Feed | Rate | GC Analysis | | percent |
|---|---|---|---|---|---|---|---|---|
| min | mL/min | bars | °C. | Wt. (g) | g/min | Area Fl* | percent Fn** | Conversion |
| 0 |  | ON |  |  |  | 11.28 | 0.00 |  |
| 46 | 28.32 | 2.76 | 25.3 | 632.2 |  | 4.26 | 7.02 | 62.23 |
| 94 | 28.32 | 2.90 | 25.8 | 554.8 | 1.61 | 2.89 | 8.39 | 74.38 |
| 154 | 28.32 | 2.90 | 24.9 | 488.1 | 1.11 | 2.30 | 8.98 | 79.61 |
| 244 | 28.32 | 2.90 | 23.9 | 405.5 | 0.92 | 2.23 | 9.05 | 80.23 |
| 314 | 28.32 | 2.90 | 25.8 | 339.8 | 0.94 | 2.1 | 9.20 | 81.56 |
| 394 | 28.32 | 2.90 | 26.1 | 264.1 | 0.95 | 1.9 | 9.38 | 83.16 |

*Fl = fluorene
**Fn = fluorenone
***2.76 bars = 276 kPa
2.90 bars = 290 kPa

EXAMPLE 17

CONTINUOUS OXIDATION USING POTASSIUM HYDROXIDE AS THE BASE; OXYGEN AT INCREASED PRESSURE IN A STAINLESS STEEL REACTOR AT AN ELEVATED TEMPERATURE: HIGH CONCENTRATION OF FLUORENE IN PYRIDINE

The reactor is a 2.54 cm diameter stainless steel tube, 182.8 cm in length and packed to a height of 152.4 cm with KOH pellets (85 percent, contains 15 percent water, A.C.S reagent grade, 758.9 g, 13.5 mole). The temperature is measured by a thermocouple inside a thermowell, which runs the entire length of the reactor. The reactor is also equipped with a gas inlet at the base to maintain a nitrogen atmosphere in the reaction solution until the reaction is begun, at which point oxygen for the reaction is delivered to the reactor. A second inlet at the base of the reactor is used to introduce the reaction mixture at a constant rate by means of a metering pump. There is a feed reservoir (10 L in volume), connected to the suction port of the metering pump. The entire apparatus is constructed of type 316 stainless steel.

The reactor is flushed with nitrogen before a solution containing 22.16 percent by weight of fluorene in pyridine is charged to the feed reservoir. The metering pump is set to pump at 1.4 mL/min and energized to begin flow of the solution to the reactor. The oxygen flow is started and adjusted to 23.60 mL/min (0.063 mole/h oxygen), as measured by a rotameter. The start of the oxygen flow is considered to be time 0 for the reaction. The exit port of the reactor is restricted to maintain the pressure within the reactor at 2.97 bars (297 kPa). The temperature, as measured by the thermocouple, is 43.1° C.

The reaction mixture is collected at the overflow of the reactor column and is sampled at intervals, as above. After 80 min, the reaction mixture contains 0.0 percent of fluorene and 22.16 percent of 9-fluorenone (100.00 percent of the original fluorene is converted to 9-fluorenone). The reaction is continued until all of the material in the feed reservoir has been consumed (194 min), sampled again and analyzed as in Example 3. The reaction mixture contains 0.18 percent of fluorene and 21.98 percent of 9-fluorenone (99.19 percent of the original fluorene is converted to 9-fluorenone. No other oxidation products are detected. Results are shown in Table V.

EXAMPLE 18

OXIDATION OF FLUORENE WITH AIR AT AMBIENT PRESSURE: 50 percent SODIUM HYDROXIDE SOLUTION The reactor described in Example 1 is used.

After the reactor is flushed with nitrogen, 50 percent aqueous sodium hydroxide solution (A.C.S. reagent grade, 195.86 g dry weight, 391.72 g of solution, 4.90 mole) is charged to the reactor followed by 100 g of fluorene concentrate (81.39 percent by weight of fluorene, 0.49 mole of fluorene) and 398 mL (406.95 g, 5.14 mole) of pyridine. The stirrer is turned on and the speed adjusted to 2000 rpm. Coolant is admitted to the cooling coil and the temperature of the reaction mixture is adjusted to 30.4° C.

Air flow is initiated and adjusted to 943.86 mL/min (0.088 mole/min) as measured by a rotometer. The initiation of air flow is time 0 for the reaction. The reaction mixture is sampled after 60 min and analyzed by gas chromatography (GC) on a Varian 3400 GC equipped with a 30 m by 0.53 mm Megabore (TM of J & W) capillary column coated with a 3-micron film of DB-624 as the stationary phase and a flame ionization detector (Varian 3400). At this point, the reaction mixture contains 63.79 percent of fluorene and 17.60 percent of 9-fluorenone (21.62 percent conversion of fluorene). At the end of 3 h, the mixture contains 14.41 percent of fluorene and 66.98 percent of 9-fluorenone (82.32 percent conversion of fluorene). At the end of 5 h, the reaction mixture contains no detectable fluorene and 81.39 percent of 9-fluorenone (100 percent conversion of fluorene). The amount of oxygen introduced into the reaction mixture during this time is 2.65 mole.

Stirring is stopped and the phases are allowed to separate. The organic phase is removed by decantation and transferred to a rotary evaporator to remove pyridine (below 0.5 percent by GC). The resulting oil is allowed to cool to 65° C. Hexane (100 mL) is added to the oil in the flask and the mixture is allowed to cool to 25° C. to crystallize 9-fluorenone. Crystalline 9-fluorenone is collected on a fritted filter and washed with hexane (100 mL). The dried crystals weigh 66.26 g (75.09 percent of theory, 99.9 percent fluorenone by GC.

This example shows that very pure fluorenone can be obtained from impure fluorene streams.

TABLE V

CONTINUOUS OXIDATION OF FLUORENE WITH OXYGEN AT ELEVATED PRESSURE AND TEMPERATURE

| Time min | $O_2$ mL/min | Press.*** kPa | Temp. °C. | Feed Wt. (g) | Rate g/min | GC Analysis Area Fl* | GC Analysis percent Fn** | percent Conversion |
|---|---|---|---|---|---|---|---|---|
| 0 | 24.3 | 297 | 43.1 | 324.2 | | | 22.16 | |
| 40 | 24.3 | 317 | 49.3 | 269.0 | 1.4 | 0.00 | 22.16 | 100.00 |
| 80 | 24.3 | 303 | 46.9 | 212.5 | 1.4 | 0.00 | 22.16 | 100.00 |
| 144 | 24.3 | 321 | 53.6 | 123.4 | 1.4 | 0.26 | 21.90 | 98.83 |
| 194 | 24.3 | 327 | 45.1 | 53.8 | 1.4 | 0.18 | 21.98 | 99.19 |

*Fl = fluorene
**Fn = fluorenone

EXAMPLE 19

OXIDATION OF FLUORENE BY AIR USING 50 percent SODIUM HYDROXIDE SOLUTION EFFECT OF IMPROVED AIR DISPERSION The reactor is a 3000-mL cylinder (200 mm diameter, 140 mm tall) equipped with a bottom drain to which is attached a centrifugal pump (March Manufacturing Model RC-2CP-MD), which discharges to a return line 11 mm in diameter. The return line carries the reaction solution to the top of the reactor. Air is fed to the reactor via a tee in the return line at about halfway up the height of the reactor. Temperature is maintained at a constant temperature by a cooled/heated bath which pumps heat exchange fluid through a jacket surrounding the reactor. The reactor is also equipped with a nitrogen inlet for maintaining a nitrogen atmosphere over the reaction mixture. The entire apparatus is constructed of fluorocarbon resin commercially available from E. I. du Pont de Nemours & Co. under the trade designation Teflon PFA.

After the reactor is flushed with nitrogen, 50 percent aqueous sodium hydroxide solution (A.C.S. reagent grade, 46.57 g dry weight, 93.14 g of solution, 1.16 mole) is charged to the reactor followed by a solution of fluorene (20 g, 0.12 mole) in pyridine (193.52 g, 189.26 mL, 2.45 mole) of pyridine. The pump is turned on and the solution is allowed to become homogeneous. Coolant is admitted to the jacket and the temperature of the reaction mixture is adjusted to 30.4° C.

Air flow is initiated and adjusted to 943.86 mL/min (0.088 mole/min) as measured by a rotometer. The initiation of air flow is time 0 for the reaction. The reaction mixture is sampled after 60 min and analyzed by gas chromatography (GC) on a Varian 3400 GC equipped with a 30 m by 0.53 mm Megabore (Trademark of J & W Scientific Inc.) capillary column coated with a 3-micron film of DB-624 as the stationary phase and a flame ionization detector (Varian 3400). At this point, the reaction mixture contains 67.23 percent of fluorene and 32.77 percent of 9-fluorenone (32.77 percent conversion of fluorene). At the end of 2.5 h, the mixture contains 15.33 percent of fluorene and 84.67 percent of 9-fluorenone (84.67 percent conversion of fluorene). At the end of 4.5 h, the reaction mixture contains no detectable fluorene and 100 percent of 9-fluorenone (100 percent conversion of fluorene). The amount of oxygen introduced into the reaction mixture during this time is 2.38 mole.

Stirring is stopped and the phases are allowed to separate. The organic phase is removed by decantation and transferred to a rotary evaporator to remove pyridine (below 0.5 percent by GC). The resulting oil is allowed to cool to 65° C. Hexane (100 mL) is added to the oil in the flask and the mixture is allowed to cool to 25° C. to crystallize 9-fluorenone. Crystalline 9-fluorenone is collected on a fritted filter. The dried crystals weigh 21.55 g (99.4 percent of theory).

EXAMPLE 20

OXIDATION OF FLUORENE WITH AIR: 50 percent SODIUM HYDROXIDE SOLUTION (STOICHIOMETRIC AMOUNT)

The reactor and procedure of Example 19 are used. To the reactor is charged 50 percent aqueous sodium hydroxide solution (A.C.S. reagent grade, 4.81 g dry, 9.62 g solution, 0.12 mole), followed by a solution of 20 g of fluorene (0.12 mole) and 180 g (2.28 mole, 176.04 mL) of pyridine. The rate of air flow is 943.86 mL/min (0.0088 mole/min of oxygen).

After 60 min, the reaction mixture contains 57.21 percent of fluorenone and 42.79 percent of 9-fluorenone (42.79 percent conversion). At the end of 120 min, the mixture contains 19.64 percent of fluorene and 80.36 percent of 9-fluorenone (80.36 percent conversion). At the end of 4 h, the mixture contains no detectable fluorene (100 percent conversion to 9-fluorenone). During the 4 h reaction period, 2.12 mole of oxygen is passed through the reactor.

The product, isolated as in the preceding example, weighs 21.71 g (100.14 percent of theory).

EXAMPLE 21

OXIDATION OF FLUORENE (50 percent SODIUM HYDROXIDE SOLUTION) WITH AIR USING 4-(N,N-DIMETHYLAMINO)PYRIDINE AS COSOLVENT The apparatus and method of Example 19 is used. To the reactor is charged 50 percent aqueous sodium hydroxide solution (A.C.S. reagent grade, 48.13 g dry, 96.26 g of solution, 1.20 mole), followed by a solution of 20 g (0.12 mole) of fluorene, 4,4-(dimethylamino)pyridine (20.0 g, 0.16 mole) and 160.00 g of pyridine (2.02 mole, 156.48 mL).

After 60 min, the reaction mixture contains 65.12 percent of fluorene and 34.88 percent of 9-fluorenone (34.88 percent conversion). After 120 min, the mixture contains 21.48 percent of fluorene and 78.52 percent of 9-fluorenone (78.52 percent conversion). At the end of 3 h, no fluorene is detected (100 percent conversion of fluorene). The air passing through the reaction mixture contains 1.59 mole of oxygen.

This example shows that use of N,N-(dimethylamino)pyridine as cosolvent decreases the time required for complete conversion of fluorene.

EXAMPLE 22

OXIDATION OF FLUORENE (50 percent SODIUM HYDROXIDE) WITH AIR USING DIPHENYLMETHANE AS COSOLVENT The reactor and method of Example 19 are used. To the reactor is charged 50 percent aqueous sodium hydroxide solution (4.87 g dry, 9.74 g of solution, 0.12 mole), followed by a solution of fluorene concentrate (48.15 percent of fluorene, 42.00 g, 0.12 mole of fluorene and 0.25 mole of diphenylmethane) and pyridine (118.0 g, 1.49 mole, 115.63 mL).

After 1 h, the reaction mixture contains 35.51 percent of fluorene and 12.64 percent of 9-fluorenone (26.25 percent conversion). After 2 h, the mixture contains 30.37 percent of fluorene and 17.78 percent of 9-fluorenone (36.93 percent conversion). At the end of 5 h, the mixture contains no detectable fluorene (complete conversion to 9-fluorenone). The amount of oxygen introduced into the reaction mixture during the 5 h reaction period is 2.65 mole.

Stirring is stopped and the phases are allowed to separate. The organic phase is removed by decantation and transferred to a rotary evaporator to remove pyridine (below 0.5 percent by GC). The resulting oil is allowed to cool to 65° C., whereupon 100 mL of a mixture of isopropanol (90 percent by weight) and water (10 percent by weight) is added to the oil in the flask and the resulting mixture is allowed to cool to 25° C. as crystals form. The crystalline fluorenone is collected on a fritted filter and washed with 100 mL of isopropanol:water (9:1 by weight). The dried crystals weigh 15.57 g (71.01 percent of theory, 99.9 percent fluorenone).

This example shows that high purity fluorenone can be obtained from impure fluorene streams.

EXAMPLE 23

CONTINUOUS PROCESS FOR THE OXIDATION OF FLUORENE TO 9-FLUORENONE

The reactor is a vertical 5.08 cm diameter pipe (fluorocarbon resin, Teflon® PFA, E. I. dupont deNemours & Co.). The reactor comprises 12 stirred sections, each 1.75 cm long, separated by horizontal spacers (0.64 cm thick) each perforated with eight holes (0.64 cm diameter) to permit communication between the sections. Centered within each stage is an impeller, mounted on a vertical drive shaft of type 316 stainless steel (0.954 cm height per section, 1.651 cm diameter). The impeller is driven by an air motor at a constant speed of 1000 rpm. Each stirred section has a volume of about 100 mL. The uppermost of the stirred sections contains a port for introduction of reactants and removal of products and a thermowell for measuring the temperature of the reactor contents. Additional thermowells are placed in stage four (from top) and just below stage six. The lowest stirred section contains a port for introduction of reactants and removal of products. At the bottom of the reactor is a tee joint, connected to a bottom drain on one leg for removal of reactor contents and to ports for introducing feed solution and oxidizing gas.

After the reactor is purged with nitrogen, pyridine (400 mL) is charged to the reactor to a level slightly above the bottom of the sixth stage. The stirrer is turned on (1000 rpm). Sodium hydroxide (50 percent by weight) is metered into the reactor at a rate of 1.26 mL/min. At the same time, fluorene in pyridine (20 percent by weight of fluorene) is fed to the first stage through a metering pump at a rate of 2.25 mL/min. The combined flow rate is 3.51 mL/min, resulting in a residence time of 5.13 h. Air and oxygen are introduced into the bottom stage in 1:1 volume ratio at a rate of 94.38 mL/min. Vent gas is released through a control valve which regulates the pressure to 2.83 bars (283 kPa). The product solution is collected at the top overflow and analyzed by GC as in Example 19.

TABLE VI

The following results are obtained:

| Time (min) | Analysis, area percent | | | Percent Conversion | Temp (°C.) | Pressure (Bars) | (kPa) |
|---|---|---|---|---|---|---|---|
| | Pyridine | Fluorene | Fluorenone | | | | |
| 0 | 79.06 | 20.74 | 0.13 | 0.00 | 47.1 | 2.83 | 283 |
| 180 | 93.34 | 0.42 | 6.17 | 97.97 | 49.2 | 2.83 | 283 |
| 255 | 92.78 | 0.19 | 6.94 | 99.08 | 48.6 | 2.90 | 290 |
| 315 | 92.12 | 0.17 | 7.63 | 99.18 | 48.0 | 2.83 | 283 |
| 375 | 91.39 | 0.15 | 8.38 | 99.28 | 48.5 | 2.83 | 283 |
| 435 | 90.99 | 0.19 | 8.73 | 99.08 | 49.8 | 2.90 | 290 |
| 495 | 90.27 | 0.18 | 9.47 | 99.13 | 47.3 | 2.97 | 297 |
| 555 | 89.47 | 0.17 | 10.28 | 99.18 | 49.0 | 3.17 | 317 |
| 805 | 87.85 | 0.14 | 11.92 | 99.32 | 50.0 | 3.31 | 331 |
| 1230 | 85.35 | 0.00 | 14.56 | 100.00 | 48.0 | 3.45 | 345 |

EXAMPLE 24

CRYSTALLIZATION STUDIES:

The organic phase from a reaction mixture is collected. Pyridine in the mixture is removed by batch distillation or using a falling film still (120° C./343 mm Hg (46 kPa)). Any water present in the organic phase is removed as an azeotrope with pyridine. After the pyridine has been removed, the crude fluorenone is cooled in a batch crystallizer to crystallize fluorenone (about 10° C.). Fluorenone is isolated by filtration. The crystalline mass is washed with a solvent and the recovery and purity of the washed crystalline mass is determined (GC). The following results are obtained:

TABLE VII

| | Pyr[a] | MC[b] | Tol[c] | IPAL[d] | hexane | none |
|---|---|---|---|---|---|---|
| SOLVENT | | | | | | |
| wt. flask | 75.72 | 71.75 | 77.54 | 75.68 | 75.24 | 71.75 |
| wt. flask + crystal mass | 114.09 | 108.78 | 114.81 | 113.38 | 112.50 | 108.78 |
| wt. crystal mass | 38.38 | 36.98 | 37.26 | 37.70 | 37.26 | 36.98 |
| wt. funnel | 36.85 | 37.95 | 38.48 | 38.53 | 38.39 | 37.95 |
| wt. funnel + crystals | 39.01 | 41.21 | 42.18 | 49.43 | 51.19 | 52.62 |
| wt. crystals[e] | 0.36 | 3.26 | 3.70 | 10.90 | 12.80 | 14.67 |
| wt. filter flask | 75.24 | 75.72 | 75.89 | 77.55 | 75.40 | 75.72 |
| wt. solvent | 39.39 | 35.43 | 32.11 | 35.34 | 39.90 | — |
| wt. filtrate[f] | 113.00 | 106.59 | 109.19 | 104.12 | 99.45 | 95.94 |
| net wt. filtrate[g] | 37.76 | 30.87 | 33.30 | 26.57 | 24.05 | 20.22 |
| COMPOSITION (percent fluorenone) | | | | | | |
| initial | 58.25 | 58.25 | 58.25 | 58.25 | 58.25 | 58.25 |
| crystals | 100.00 | 100.00 | 100.00 | 100.00 | 100.00 | 90.02 |
| filtrate | 54.70 | 53.87 | 50.68 | 35.51 | 28.11 | 27.06 |
| wt. fluorenone | 22.36 | 21.54 | 21.70 | 21.96 | 21.70 | 21.54 |
| percent fluorenone recovered | 1.61 | 15.13 | 17.05 | 49.64 | 58.98 | 68.10 |
| as percent recovered without washing | 2.36 | 22.22 | 25.03 | 72.89 | 86.60 | 100.00 |

[a]pyridine
[b]methylene chloride
[c]toluene
[d]isopropanol
[e]washed
[f]dry
[g]dry These experiments show that washing the crystalline mass with either of hexane or isopropanol gives the best recovery of very high purity fluorenone.

EXAMPLE 25

OXIDATION METHOD USING 50% POTASSIUM HYDROXIDE SOLUTION AS THE BASE.

The reactor is a 300 mL cylinder 62 mm in diameter by 100 mm tall equipped with a 38 mm diameter turbine impeller driven by a vertical shaft Parr Model 4841 available from the Parr Instrument Company, Moline, Ill. Stirring rate is measured by a tachometer. Temperature is controlled by a Parr temperature controller Model 4841 available from the Parr Instrument Company, Moline, Ill.

The temperature is measured by a thermocouple inside a thermowell which runs the entire depth of the reactor. The reactor is also equipped with a nitrogen inlet which is used to maintain a nitrogen atmosphere above the reaction solution. The apparatus is constructed of Hastaloy C.

The reactor is flushed with nitrogen, then KOH (50% aqueous, A.C.S reagent grade, 77.42 g solution weight, 0.69 mole) followed by a solution consisting of fluorene concentrate (57% fluorene, 20.12 g, contains 0.07 mole fluorene) and pyridine (45.87 g, 0.58 mole, 44.86 mL) is charged to the reactor. The stirrer is started and the speed adjusted to 550 rpm. The temperature controller is switched on and the temperature of the reaction solution is adjusted to 40° C. The air flow is started and adjusted to 0.2 SCFH (standard cubic feet per hour, 94 mL/min at atmospheric pressure and 25° C., 0.00088 moles/min of contained oxygen.) as measured by a rotometer. The vent gas is released through a control valve which regulates the pressure in the reactor to 70 psig (5.8 bars, 580 kPa) absolute). The start of the air flow is considered to be time 0 for the reaction.

The reaction mixture is sampled after 60 minutes and analyzed by gas chromatography (GC) on a Varian 3400 GC equipped with a 30 meter by 0.53 mm Megabore (Trademark of J & W Scientific Inc.) which is a capillary column coated with a 3 micron film of DB-624 as the stationary phase and a flame ionization detector (FID)(Varian 3400). This analysis shows that 21.20% of the starting fluorene has been converted to fluorenone. The reaction is sampled again after three hours and analyzed as before which shows that 74.26% of the starting fluorene has now been converted to fluorenone. The reaction is sampled again after five hours and analyzed as before which shows that the reaction mixture now contains no detectable fluorene for 100% conversion of the starting fluorene to 9-fluorenone. An amount, 0.265 moles, of oxygen was contained in the air passed through the reactor during the five hour reaction time.

The stirring is stopped and the phases allowed to separate. The organic phase is decanted and placed on the rotary evaporator where the pyridine is removed to less than 0.5% of the mass by GC. The resulting oil is allowed to cool to 65° C. then cyclohexane (20 mL) is added to the flask and the mixture allowed to cool to 25° C. as crystals form. The crystals of fluorenone are collected on a fritted filter, then washed with an additional portion of cyclohexane (10 mL), and dried in a vacuum oven. The dried crystals weigh 9.69 g or 78.01% of theory (12.43 g) and analyze as 99.9% fluorenone.

This method allows for the isolation of very pure fluorenone from impure fluorene streams.

EXAMPLE 26

SELECTIVITY OF OXIDATION METHOD IN PRODUCING VERY HIGH PURITY (>99.6%) BHPF FROM A CRUDE FLUORENE CONCENTRATE (60% FLUORENE).

A sample of starting material contains 60% fluorene by GC analysis. This crude fluorene concentrate (50.54 g, contains 0.18 mole) is dissolved in pyridine (282.72 g, 3.57 mole) to give a 9.1% weight/weight solution in pyridine. The reactor described in Example 1 is used.

The solution of starting material in pyridine is stirred at 500 rpm in the presence of solid sodium hydroxide pellets (29.0 g, 0.73 mole) while oxygen is bubbled through it at a rate of 0.1 SCFH (standard cubic feet per hour, 47 ml/min., 0.0021 moles/min.of oxygen.). After three hours, the reaction mixture is sampled and analyzed by gas chromatography (GC) on a Varian 3400 GC equipped with a 30 meter by 0.53 mm Megabore (Trademark of J&W) capillary column coated with a 3 micron film of DB-624 as the stationary phase and a flame ionization detector (FID)(Varian 3400). No fluorene is detectable in the mixture. The reaction mixture is stripped of the pyridine, and 31.5 g of the resulting fluorenone containing solids (contains 0.113 mole fluorenone) are dissolved in phenol to give a molar ratio of phenol (85.50 g, 0.91 mole) to fluorenone of 8 to 1.

Without isolation the fluorenone in the reaction product mixture is converted to bis(hydroxyphenyl)phenyl fluorene (BHPF) by adding 3-mercaptopropanesulfonic acid (MPSA, 1.293 g, 7.3 mole % relative to the fluorenone) to initiate the reaction which is allowed to proceed for 3 hours at 40° C. The reaction mixture is then washed five times with water (equal volumes). The mixture is analyzed quantitatively as 49.7% phenol and 23.2% BHPF.

A portion, 71.3 g, of the resulting mixture is distilled to remove the phenol until a weight ratio of phenol to BHPF of 0.9 to 1 is obtained in the still pot. The distillation residue is diluted with three times its weight of methylene chloride which forms a homogeneous mixture that soon begins to form crystals. After 2 hours, the crystals are collected by filtration. These crystals are washed twice with methylene chloride and once with water, then dried in an oven leaving pure white crystals (8.62 g) of BHPF. These crystals are analyzed by HPLC and shown to be 99.8% p,p-BHPF. The recovered yield s 57.2% based on fluorenone.

EXAMPLE 27

THIS EXAMPLE OF OUR OXIDATION METHOD SHOWS THE UTILITY OF THIS VERY SELECTIVE OXIDATION METHOD IN PRODUCING VERY HIGH PURITY (>99.6%) BHPF FROM A CRUDE FLUORENE CONCENTRATE (80% FLUORENE).

The reactor described in Example 1 is flushed with nitrogen, then NaOH (50% aqueous, A.C.S reagent grade, 76.5 g dry weight, 153.0 g solution weight, 1.91 mole) followed by a solution consisting of fluorene concentrate (fluorene concentrate containing 80% fluorene obtained from Deza Corporation, Valasske Meririci, Czech Republic) (100.0 g concentrate, 0.48 mole) and pyridine (300.0 g, 3.79 mole, 307 ml) is charged to the reactor. The stirrer is started and the speed adjusted to 1000 rpm. Coolant is admitted to the coils, and the temperature of the reaction solution is adjusted to 42° C. The oxygen flow is started and adjusted to 0.2 SCFH (standard cubic feet per hour, 94.38 ml/min. at 25° C. and atmospheric pressure, 0.0042 moles/min.of oxygen.) as measured by a rotometer. The start of the oxygen flow is considered to be time 0 for the reaction.

The reaction mixture is sampled after 60 minutes and analyzed by gas chromatography (GC) on a Varian 3400 GC equipped with a 30 meter by 0.53 mm Megabore (Trademark of J & W Scientific Inc.) capillary column coated with a 3 micron film of DB-624 as the stationary phase and a flame ionization detector (FID)(Varian 3400). This analysis shows that 55.47% of the starting fluorene has been converted to fluorenone. The reaction is sampled again after three hours and analyzed as before which shows that 99.46% of the starting fluorene has now been converted to fluorenone. The reaction is sampled again after 4.5 hours and analyzed as before which shows that the reaction mixture now contains no detectable fluorene for 100% conversion of the starting fluorene to 9-fluorenone. No other products of oxidation are detected. 1.14 moles of oxygen have been passed through the reactor during the four hour 30 minute reaction time.

Stirring is stopped and the phases allowed to separate. The organic phase is decanted and placed on the rootary evaporator where the pyridine is removed to less than 0.5% of the mass as determined by GC analysis. The resulting oil is allowed to cool to 25° C.

Without purification, a portion (16.05 g, containing 0.0713 mole fluorenone) of the oxidate is added to a reaction flask containing phenol (67.05 g, 0.713 mole) at 45° C. The mixture is stirred while 3-mercaptopropanesulfonic acid (0.90 g, 0.00577 mole) is added at once. The temperature is adjusted to 55° C. and maintained at this point for eight hours. The reaction mixture is then extracted (6×80 ml) with water to remove the catalyst. The resulting mixture amounts to 63 g which is added to a 250 ml round bottom flask and heated until the mixture is a homogeneous solution. The mixture is analyzed quantitatively as 45.5% phenol and 38.9% BHPF.

Methylene chloride (122 g) is added and the mixture heated to dissolve solids. All but a few small clumps dissolve. More methylene chloride (113 g) is added to help dissolve remaining solids then the mixture is passed through a paper filter to remove excess solids. The mixture is then allowed to cool to room temperature while stirring and crystallization is observed.

The brown slurry, 208 g, is poured into a medium frit filter and filtered by suction. When the filtrate is reduced to a slow drip the filtration is stopped. An amount, 160 g, of brown filtrate is recovered. The resulting cake is yellow/green in color. Methylene chloride (56 g) is slowly added to the top of the cake, and the cake is displacement washed. Washing improved the color greatly.

The wet cake is analyzed by liquid chromatography (LC) and determined to be comprised of 99.6% p,p-BHPF relative to isomers, adducts and other hydrocarbons (excluding methylene chloride).

The cake is placed in a vacuum oven at 85°–90° C. for drying. Recovered product: 5.9 g.

Yield =(5.9/24.6)×100=24%.

This example of our oxidation method shows the utillity of this very selective oxidation method in producing very high purity (>99.6%) BHPF from a crude fluorene concentrate (80% fluorene).

EXAMPLE 28

SELECTIVITY OF OXIDATION METHOD IN PRODUCING VERY HIGH PURITY (>99.8%) BHPF FROM A CRUDE FLUORENE CONCENTRATE (80% FLUORENE).

The reactor described in Example 1 is flushed with nitrogen, then NaOH (50% aqueous, A.C.S reagent grade, 76.5g dry weight, 153.0 g solution weight, 1.91 mole) followed by a solution consisting of fluorene concentrate (fluorene concentrate containing 80% fluorene obtained from Rutgers-VfT AG, Kekulestase 30, D-44579 Castro-pRauxel, Germany) (100.0 g concentrate, 0.48 mole) and pyridine (300.0 g, 3.79 mole, 307 ml) is charged to the reactor. The stirrer is started and the speed adjusted to 1000 rpm. The coolant is admitted to the coils and the temperature of the reaction solution is adjusted to 42° C. The oxygen flow is started and adjusted to 0.2 SCFH (standard cubic feet per hour, 94.38 ml/min. at 25° C. and atmospheric pressure, 0.0042 moles/min.of oxygen.) as measured by a rotometer. The start of the oxygen flow is considered to be time 0 for the reaction. The reaction mixture is sampled after 60 minutes and analyzed by gas chromatography (GC) on a Varian 3400 GC equipped with a 30 meter by 0.53 mm Megabore (Trademark of J & W Scientific Inc.) capillary column coated with a 3 micron film of DB-624 as the stationary phase and a flame ionization detector (FID-)(Varian 3400). This analysis shows that 71.04% of the starting fluorene has been converted to fluorenone. The reaction is sampled again after three hours and analyzed as before which shows that 98.58% of the starting fluorene has now been converted to fluorenone. The reaction is sampled again after 3.5 hours and analyzed as before which shows that the reaction mixture now contains no detectable fluorene for 100% conversion of the starting fluorene to 9-fluorenone. No other products of oxidation are detected. An amount, 0.88 moles, of oxygen are passed through the reactor during the 3 hour 30 minute reaction time.

The stirring is stopped and the phases allowed to separate. The organic phase is decanted and placed on the rotary evaporator where the pyridine is removed to less than 0.5% of the mass as determined by GC. The resulting oil is allowed to cool to 25° C.

Without purification, a portion (16.10 g, containing 0.0715 mole fluorenone) of the oxidate is added to a reaction flask containing phenol (67.26 g, 0.715 mole) at 45° C. The mixture is stirred while 3-mercaptopropanesulfonic acid (0.90 g, 0.00577 mole) is added at once. The temperature is adjusted to 55° C. and maintained at this point for eight hours. The reaction mixture is then extracted (6 ×80 ml) with water to remove the catalyst. The resulting mixture amounts to 59.6 g which is added to a 250 ml round bottom flask and heated until the mixture is a homogeneous solution. The mixture is analyzed quantitatively as 45.6% phenol and 35.5% BHPF (phenol:BHPF mass ratio=1.28).

100 g of methylene chloride are added to the mixture to form a homogeneous solution. Upon cooling to room temperature no precipitate was evident. An amount, 60 ml, deionized(DI) water are added and the mixture is distilled to remove the methylene chloride water and phenol. When the temperature of the mixture is 137° C., the mixture is allowed to cool. Analysis of the mixture indicates a phenol:BHPF mass ratio of 1:1. When the mixture is approximately 80° C., approximately 100 g methylene chloride is added resulting in mild refluxing and rapid cooling. As the mixture approaches room temperature, it is seeded with BHPF crystals. Within 2 hours, more crystals are evident. The mixture is allowed to stir at room temperature overnight. The brown slurry, weight 80 g, is poured into a medium frit filter and filtered by suction. When the filtrate is reduced to a slow drip the filtration is stopped. The resulting cake is mustard in color. Methylene chloride (44 g) is slowly added to the top of the cake and the cake is displacement washed. Washing improved the color greatly. Another 36 g sample of methylene chloride is used to wash the cake.

The wet cake is analyzed by LC and determined to be comprised of 99.8% p,p-BHPF relative to isomers, adducts and other hydrocarbons (excluding methylene chloride).

The cake is placed in a vacuum oven at 85°–90° C. for drying. Recovered product: 6.4 g.

Yield =(6.4/21.16)×100=30.24%.

This example of the oxidation method of the invention shows the utillity of this very selective oxidation method in producing very high purity (>99.8%) BHPF from a crude fluorene concentrate (80% fluorene).

EXAMPLE 29

EFFECTS OF MIXING

The procedure of Example 25 is repeated with a impeller tp speed of 1.09 meters/sec using a Lightnin™ LabMaster II™ Model TSM2010 Mixer commercially available from Mixing Equipment Company, Avon Division, a unit of General Signal which directly measures the watts input into the mixer and the ratio of organic phase to aqueous phase volumes indicated in Table VIII. Measurements of the percent conversion of fluorene to fluorenone were taken at the times indicated in Table VIII with the impeller in the aqueous or organic phase as indicated. The results indicated in Table VIII.

TABLE VIII

| time (min.) | impeller in organic percent conversion | impeller in aqueous percent conversion | impeller in organic percent conversion | impeller in organic percent conversion |
|---|---|---|---|---|
| 0.00 | 0.00 | 0.00 | 0.00 | 0.000 |
| 60.00 |  | 3.68 | 21.20 | 33.22 |
| 120.00 | 76.23 | 5.29 | 45.42 | 52.85 |
| 180.00 |  | 9.45 | 74.26 | 70.16 |
| 240.00 | 98.28 | 13.04 | 89.07 |  |
| 300.00 |  | 18.87 | 91.51 |  |
| 360.00 |  |  | 100.00 |  |
| Organic to Aqueous phase ratio | 1.26 | .79 | 1.26 | 10 |

EXAMPLE 30

THE EFFECT OF STIRRING AT ATMOSPHERIC PRESSURE

The procedure of Example 29 is repeated using air as oxidizing gas at atmospheric pressure, with an organic to aqueous phase volume ratiio of 1.26:1 and an impeller tip speed of 5.23 m/sec. Results are shown in Table IX.

TABLE IX

| time | aqueous phase percent conversion | organic phase percent conversion |
|---|---|---|
| 0 | 0.00 | 0.00 |
| 30 | 2.60 | 19.77 |
| 60 | 4.45 | 41.98 |
| 120 | 9.41 | 78.43 |
| 240 | 19.41 | 92.37 |
| 300 | 24.26 | 100.00 |
| 360 | 29.16 | 100.00 |

Examples 29 and 30 show: The organic to aqueous phase ratio appears to have little affect on the reaction rate (compare the ratios of the two fastest runs in Table VIII) as long as the organic phase is the continuous phase. This means that a very small aqueous phase can be used and thus increase the capacity of the oxidation reactor.

Good mixing is important for rapid reaction. For instance at a mole ratio of potassium hydroxide to fluorene of 1.8:1; mole ratio pyridine to fluorene of 8.4:1.0 and air flow rate of 0.008826 Moles/Minute at 40° C. the following conversions are achieved for the given times, indicating the importance of mixing on the rate of conversion of fluorene.

TABLE X

| time (minutes) | 700 RPM corresponding to 1.35 W/L* % conversion | 1500 RPM corresponding to 19.70 W/L* % conversion | 2000 RPM corresponding to 47.21 W/L* % conversion |
|---|---|---|---|
| 0 | 0.00 | 0.00 | 0.00 |
| 15 | 5.07 | 15.17 | 20.81 |
| 30 | 20.53 | 30.13 | 39.97 |
| 45 | 30.76 | 47.02 | 56.66 |
| 60 | 48.62 | 64.52 | 85.87 |
| 90 | 62.58 | 87.56 | 95.51 |
| 120 | 74.22 | 97.40 | 99.28 |
| 150 | 81.16 | 99.60 | 99.99 |
| 180 | 87.64 | 99.94 | |
| 240 | 89.24 | 100.00 | |

*W/L = Watts/Liter

The preceding examples can be repeated with similar success by substituting the generically or specifically described reactants and/or operating conditions of this invention for those used in the preceding examples.

From the foregoing description, one skilled in the art can easily ascertain the essential characteristics of this invention and without departing from the spirit and scope thereof, can make various changes and modifications of the invention to adapt it to various usages and conditions.

The process of the invention is advantageous over oxidation processes involving phase transfer catalysts. Phase transfer catalysts, especially quaternary ammonium phase transfer catalysts, are known by those skilled in the art to degrade under oxidation conditions. Because the phase transfer catalysts degrade, their concentration decreases during a reaction; therefore, especially in continuous reactions, phase transfer catalysts either must be used in excess or must be added as reaction progresses to maintain a sufficient concentration. Furthermore, degradation of phase transfer catalyst produces by-products which make purification of the desired oxidation product (e.g. fluorenone) more difficult than it would be in the absence of such by-products.

We claim:

1. A process for the oxidation of a fluorene compound to a corresponding fluorenone compound, comprising treating the fluorene compound with an oxidizing gas in the presence of a solid alkali metal or alkaline earth metal oxide or hydroxide or a concentrated aqueous solution thereof, containing a maximum of 50% to 75% by weight of water, in a reaction mixture containing a heterocylic nitrogenous solvent, wherein the reaction mixture is free of a phase transfer agent, for a time sufficient and at a temperature sufficient to convert the fluorene compound to the fluorenone compound.

2. The process of claim 1, wherein the heterocyclic nitrogenous solvent has a solubility in water above about 20 g/100 mL at 25° C.

3. The process of claim 2, wherein the solvent is pyridine, a picoline or a lutidine.

4. The process of claim 2, wherein the solvent is pyridine.

5. The process of claim 1, wherein the oxidizing gas is air.

6. The process of claim 1, wherein the oxidizing gas is oxygen.

7. The process of claim 1, carried out under pressures from about 1 bar to about 10 bars.

8. The process of claim 1, wherein the fluorene compound is fluorene and the fluorenone compound is 9-fluorenone.

9. The process of claim 1, wherein the alkali metal hydroxide is sodium hydroxide or potassium hydroxide.

10. The process of claim 9, wherein the sodium hydroxide or potassium hydroxide is in the form of a concentrated aqueous solution.

11. The process of claim 10 wherein the concentrated aqueous solution is at least about 40 percent by weight sodium hydroxide or potassium hydroxide.

12. The process of claim 10, wherein the sodium or potassium hydroxide solution is a saturated aqueous solution.

13. The process of claim 10, carried under conditions such that the reaction mixture separates into two liquid phases.

14. The process of claim 9, wherein the sodium hydroxide or potassium hydroxide is in a solid form.

15. The process of claim 14, wherein the solid contains a maximum of about 20 percent by weight of water.

16. The process of claim 1, wherein the alkali metal or alkaline earth metal oxide or hydroxide is sodalime.

17. The process of claim 1, carried out at a temperature from about 10° C. to about 65° C.

18. The process of claim 1, carried out in batch mode in the presence of solid sodium hydroxide or potassium hydroxide, wherein the nitrogenous heterocyclic solvent is pyridine.

19. The process of claim 17, carried out in batch mode in the presence of sodium hydroxide or potassium hydroxide pellets or powder, wherein the nitrogenous heterocyclic solvent is pyridine.

20. The process of claim 1, wherein the fluorene compound is in the form of a crude concentrate, containing fluorene or substituted fluorenes, and a resulting product contains fluorenone or substituted fluorenones.

21. The process of claim 1, carried out in continuous mode in a column packed with sodium hydroxide in a solid form or potassium hydroxide pellets, wherein the oxidizing gas is oxygen.

22. The process of claim 21, wherein the column in packed with potassium hydroxide pellets, the oxidizing gas is present under a pressure from ambient to about 10 bars (1000 pKa), the heterocyclic nitrogenous solvent is pyridine, the fluorene compound is fluorene or a crude fluorene concentrate and the temperature is from about 20° C. to about 45° C.

23. The process of claim 1, carried out in continuous mode, wherein a solution of fluorene compound in heterocyclic nitrogenous solvent is contacted with a concentrated aqueous solution of alkali metal hydroxide.

24. The process of claim 23, carried out in continuous mode in a stirred reactor, wherein a solution of fluorene or crude fluorene concentrate in pyridine is contacted in countercurrent flow mode with an aqueous solution of at least 40 percent by weight of sodium or potassium hydroxide at a temperature from about 40° C. to about 65° C.

25. The process of claim 24, wherein the oxidizing gas is a mixture of air and oxygen.

26. The process of claim 1 wherein the oxidizing gas is introduced under pressure into a stirred reactor containing a continuous organic phase containing droplets of aqueous sodium or potassium hydroxide wherein the aqueous solution is at least about 40 percent by weight potassium hydroxide; the oxidizing gas is air, and the temperature is from about 40° C. to about 65° C.

27. The process of claim 1, including the further steps of removing heterocyclic nitrogenous solvent from a resulting crude product and cooling a resulting residue to crystallize the fluorenone therefrom.

28. The process of claim 26, including the further step of washing the thus-crystallized fluorenone with hydrocarbon solvent, or an alcohol solvent or mixture thereof.

29. The process of claim 28 wherein the solvent is hexane, cyclohexane, isopropanol, methanol or ethanol.

30. The process of claim 1 wherein there is mixing at a power of at least about 0.8 W/l.

31. The process of claim 30 wherein the power is at least about 15.0 W/l.

* * * * *